(12) United States Patent
Parker

(10) Patent No.: US 8,235,996 B2
(45) Date of Patent: Aug. 7, 2012

(54) ACETABULAR REAMER

(75) Inventor: Brad A. Parker, Warsaw, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 12/974,878

(22) Filed: Dec. 21, 2010

(65) Prior Publication Data

US 2011/0092974 A1    Apr. 21, 2011

Related U.S. Application Data

(62) Division of application No. 11/387,532, filed on Mar. 23, 2006, now Pat. No. 7,871,412.

(51) Int. Cl.
*A61B 17/00* (2006.01)
(52) U.S. Cl. .............. 606/81; 606/80; 606/79
(58) Field of Classification Search ............... 623/22.21, 623/22.22, 22.23, 22.24, 22.25, 22.26, 22.27, 623/22.28, 22.29, 22.3, 22.31, 22.32, 22.33, 623/22.34, 22.35, 22.36, 22.37, 22.38, 22.39, 623/22.4, 22.41, 22.42, 22.43, 22.44, 22.45, 623/22.46, 23.11, 23.12, 23.13; 606/79, 606/80, 81, 180, 86 R
See application file for complete search history.

(56) References Cited

U.S. PATENT DOCUMENTS

| | | | |
|---|---|---|---|
| 5,116,165 A | 5/1992 | Salyer | |
| 5,755,719 A | 5/1998 | Frieze et al. | |
| 5,976,148 A | 11/1999 | Charpenet et al. | |
| 6,129,732 A | 10/2000 | Lechot | |
| 6,221,076 B1 | 4/2001 | Albrektsson et al. | |
| 6,730,094 B2 | 5/2004 | Salyer et al. | |
| 6,860,903 B2 | 3/2005 | Mears et al. | |
| 7,220,264 B1 | 5/2007 | Hershberger | |

(Continued)

FOREIGN PATENT DOCUMENTS

WO     03086208 A1    10/2003

(Continued)

OTHER PUBLICATIONS

Documents form Internet site of Dictionary.com provided by Examiner with Office Action dated Feb. 17, 2009 in U.S. Appl. No. 11/387,532 (10 pages); specifically, five of the pages are from http://dictionary.reference.com/browse/hemisphere and five of the pages are from http://dictionary.reference.com/browse/sphere.

*Primary Examiner* — Eduardo C Robert
*Assistant Examiner* — Jan Christopher Merene
(74) *Attorney, Agent, or Firm* — Taylor IP, P.C.

(57) ABSTRACT

A method of reaming an acetabulum includes the steps of: providing an acetabular reamer including a partially hemispherical shell having a shell radius, and a base including a first circumferential base segment and a second circumferential base segment, the shell including a first part on one side of the first circumferential base segment and the second circumferential base segment, and a second part on another side of the first circumferential base segment and the second circumferential base segment, the acetabular reamer further including a first non-planar surface connected to the first part, the first non-planar surface having a first curvature not equal to the shell radius, and a second non-planar surface connected to the second part, the second non-planar surface having a second curvature not equal to the shell radius; connecting the acetabular reamer to a driver; and reaming the acetabulum.

2 Claims, 3 Drawing Sheets

U.S. PATENT DOCUMENTS

| | | |
|---|---|---|
| 7,621,915 B2 | 11/2009 | Frederick et al. |
| 7,850,692 B2 * | 12/2010 | White et al. ............... 606/81 |
| 7,896,881 B2 * | 3/2011 | Cutshall et al. ............ 606/81 |
| 7,901,406 B1 * | 3/2011 | Lechot ....................... 606/81 |
| 8,052,689 B2 * | 11/2011 | Sherry et al. ............... 606/81 |
| 2002/0099380 A1 | 7/2002 | Salyer et al. |
| 2003/0130741 A1 | 7/2003 | McMinn |
| 2003/0163135 A1 | 8/2003 | Hathaway |
| 2003/0220647 A1 | 11/2003 | McCallum et al. |
| 2004/0097947 A1 | 5/2004 | Wolford et al. |
| 2004/0143271 A1 | 7/2004 | Wolford |
| 2004/0225294 A1 | 11/2004 | Frederick et al. |
| 2004/0249383 A1 | 12/2004 | White et al. |
| 2005/0075639 A1 | 4/2005 | Lechot |
| 2005/0203525 A1 * | 9/2005 | White et al. ............... 606/80 |
| 2007/0225723 A1 | 9/2007 | Berthusen |

FOREIGN PATENT DOCUMENTS

| | | |
|---|---|---|
| WO | 2004024007 A1 | 3/2004 |
| WO | 2004071310 A1 | 8/2004 |

\* cited by examiner

ACETABULAR REAMER

CROSS REFERENCE TO RELATED APPLICATIONS

This is a division of U.S. patent application Ser. No. 11/387,532, entitled "A MINIMALLY INVASIVE ORTHOPAEDIC CUTTING TOOL", filed Mar. 23, 2006, which is incorporated herein by reference. U.S. patent application Ser. No. 11/387,532 is now U.S. Pat. No. 7,871,412.

BACKGROUND OF THE INVENTION

1. Field of the Invention

The present invention relates to orthopaedic cutting tools, and, more particularly, to acetabular reamers.

2. Description of the Related Art

Minimally invasive surgical techniques have the advantage of reducing the trauma to tissue surrounding the surgical site during a surgical procedure. The small incision that surgeons are using for minimally invasive hip surgery make it difficult to insert a current full size hemispherical acetabular reamer through the small incision. However, the full size hemispherical acetabular reamer cuts a full hemispherical shape in the acetabulum with minimal wobbling and therefore provides an excellent preparation for the hip joint prosthesis. Additionally, a reamer is required to be connected to a driver, which is in turn connected to a rotational tool. The driver has a specific structure at the proximal (to the surgical site) end thereof, which is compatible with specific attachment mechanisms on the reamers. The drivers represent an investment on the part of the medical institution where the surgery is performed, and if the reamer is modified to be more compatible with minimally invasive surgical techniques, the driver attachment mechanism may be correspondingly modified, which necessitates the purchase of both the driver and the reamer for the medical institution. The purchase of a driver adds cost to the acquisition of the new reamer technology.

Orthopaedic reamers are known that cut off opposing segments of the hemispherical shell of the reamer. The resulting reamer, while having a reduced profile in a certain orientation, is no longer rotationally symmetric. The lack of rotational symmetry can cause vibration and wobbling of the reamer when in use. Such a cut-down reamer design can cut an irregular cavity in the acetabulum, for example, during hip joint replacement surgery. An irregular cavity in the acetabulum can reduce the expected lifetime of the hip joint prosthesis, cause discomfort for the patient and increase the wear in the artificial joint, among other problems. Additionally, a purpose of the hemispherical shell is that it provides a debris retaining cavity for cut material, thereby minimizing the surgical site contamination with the cut material from the acetabulum. By simply cutting off the sides of the reamer, such a reamer no longer provides a debris retaining cavity. Further, these reamers lose rigidity, which reduces the cutting performance of the reamer, and the reliability. Yet further, these reamers are relatively difficult to manufacture.

An acetabular reamer is known in which the shape of the reamer is modified in that one or more sides of the reamer are removed, and replaced with flat side surfaces which maintain the closed nature of the interior cavity. However, such a reamer creates stress points at the juncture of flat surfaces and the curved shell which can lead to cracks and failure of the reamer. Further, such a reamer is relatively difficult to manufacture.

What is needed in the art is an acetabular reamer with a reduced profile which includes a debris retaining capability, which cuts well, and which is relatively easy and cost effective to manufacture.

SUMMARY OF THE INVENTION

The present invention provides an orthopaedic cutting tool with a partially hemispherical shell which has a shell radius, a first non-planar surface and a second non-planar surface, where each of the non-planar surfaces includes curvatures which are not equal to the shell radius.

The invention comprises, in one form thereof, an orthopaedic cutting tool which includes a partially hemispherical shell having a shell radius, and a base including a first circumferential base segment and a second circumferential base segment. The shell has a first part on one side of the first circumferential base segment and the second circumferential base segment, and a second part on another side of the first circumferential base segment and the second circumferential base segment. A first non-planar surface is connected to the first part, and the first non-planar surface has a first curvature not equal to the shell radius. A second non-planar surface is connected to the second part, and the second non-planar surface has a second curvature not equal to the shell radius.

The invention comprises, in another form thereof, an orthopaedic assembly which includes a driver and an orthopaedic cutting tool connected to the driver. The orthopaedic cutting tool includes a partially hemispherical shell having a shell radius, and a base including a first circumferential base segment and a second circumferential base segment. The shell has a first part on one side of the first circumferential base segment and the second circumferential base segment, and a second part on another side of the first circumferential base segment and the second circumferential base segment. A first non-planar surface is connected to the first part, and the first non-planar surface has a first curvature not equal to the shell radius. A second non-planar surface is connected to the second part, and the second non-planar surface has a second curvature not equal to the shell radius.

The invention comprises, in yet another form thereof, a method of reaming an acetabulum, including the steps of: providing an acetabular reamer including a partially hemispherical shell having a shell radius, and a base including a first circumferential base segment and a second circumferential base segment. The shell has a first part on one side of the first circumferential base segment and the second circumferential base segment, and a second part on another side of the first circumferential base segment and the second circumferential base segment. A first non-planar surface is connected to the first part, and the first non-planar surface has a first curvature not equal to the shell radius. A second non-planar surface is connected to the second part, and the second non-planar surface has a second curvature not equal to the shell radius; connecting the acetabular reamer to a driver; and reaming the acetabulum.

An advantage of the present invention is that it provides an orthopaedic cutting tool for a minimally invasive surgical procedure.

Another advantage of the present invention is that it provides an orthopaedic cutting tool for a minimally invasive surgical procedure which maintains a debris retaining cavity.

Yet another advantage of the present invention is that it cuts well and, in particular, provides a good preparation of an acetabulum.

Yet another advantage of the present invention is that it is relatively easy and cost effective to manufacture.

Yet another advantage of the present invention is that it is compatible with existing driver attachment mechanisms.

Yet another advantage of the present invention is that it is compatible with existing drivers.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
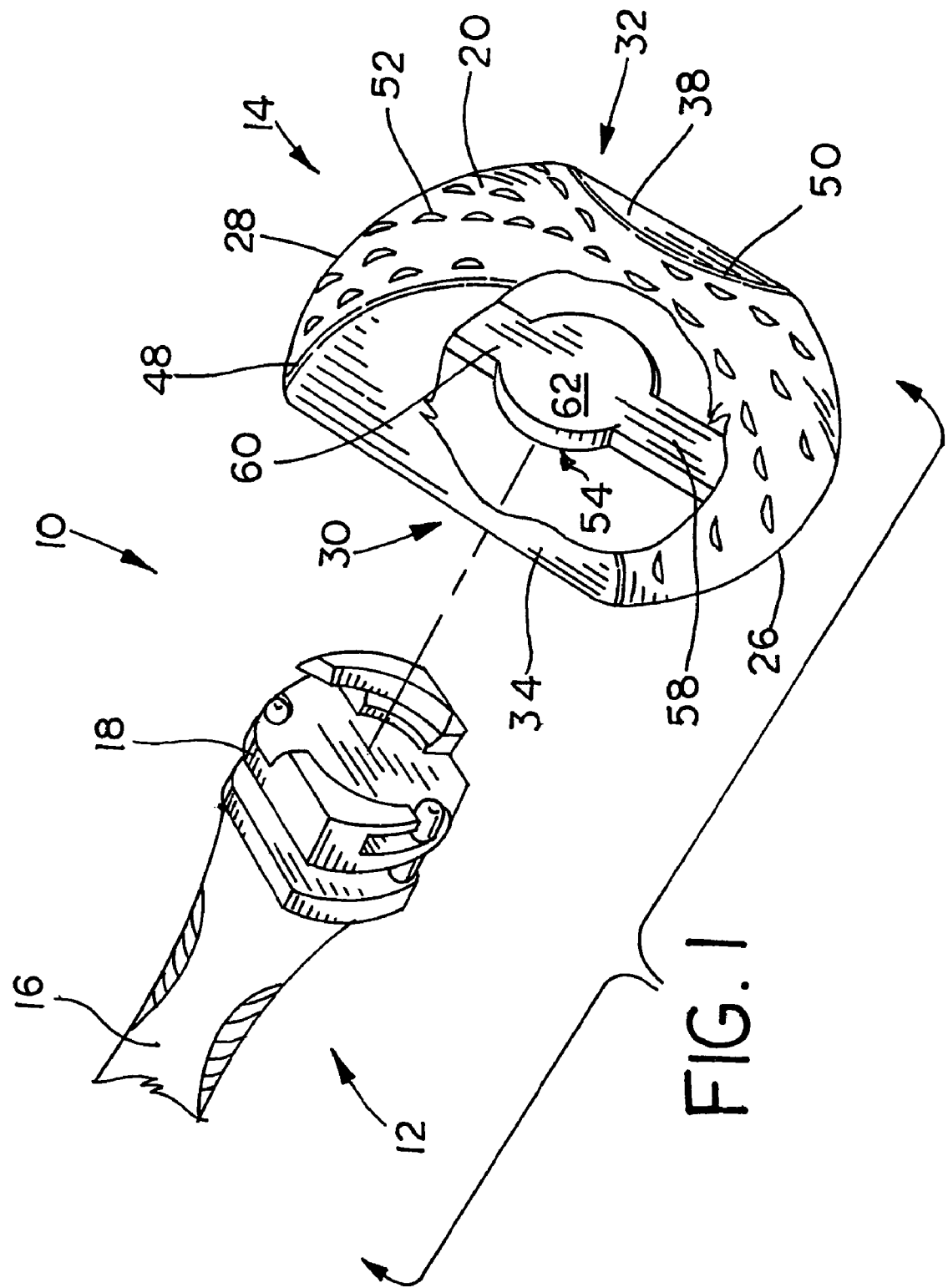
FIG. 1 is an exploded, fragmentary perspective view of an embodiment of an orthopaedic assembly according to the present invention.
Figure 2:
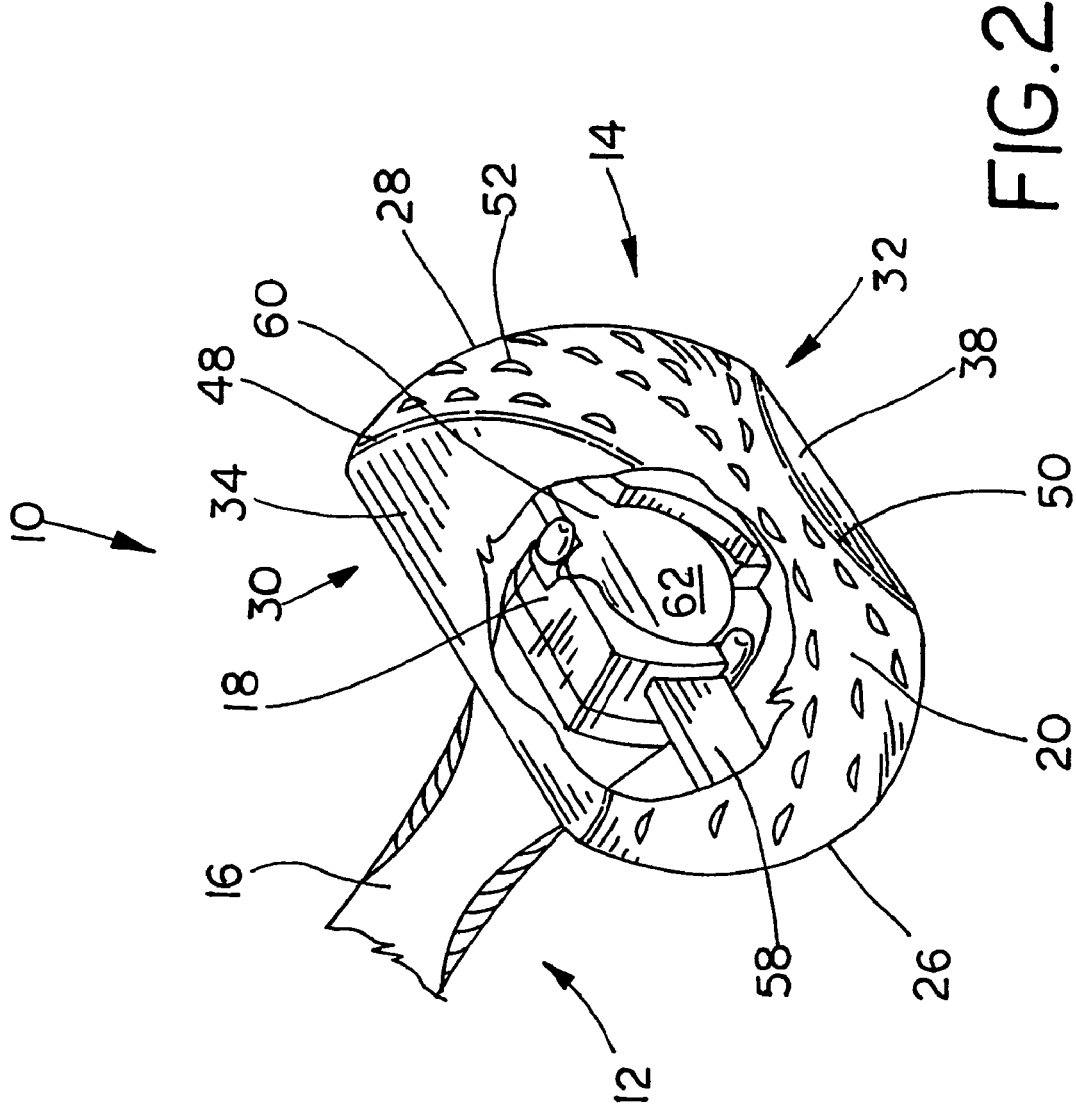
FIG. 2 is an assembled, fragmentary perspective view of the embodiment of FIG. 1.
Figure 4:
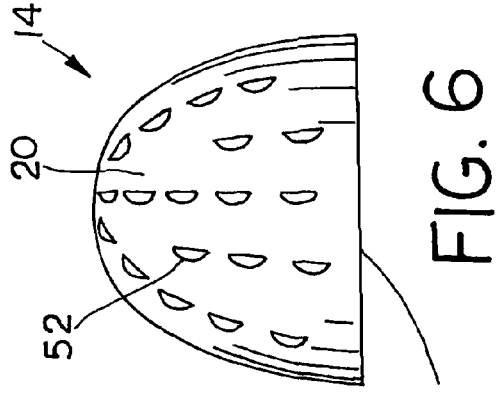
FIG. 4 is a cross-sectional view taken along section line 4-4 in FIG. 3.
Figure 6:
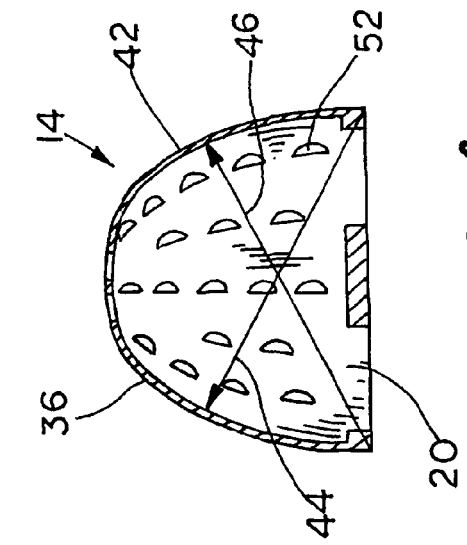
FIG. 6 is an end view of the orthopaedic cutting tool of FIG. 1.
Figure 3:
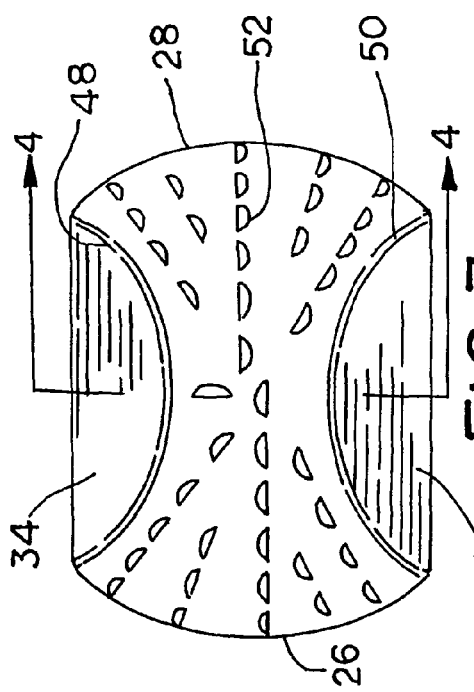
FIG. 3 is a top view of the orthopaedic cutting tool of FIG. 1.
Figure 5:
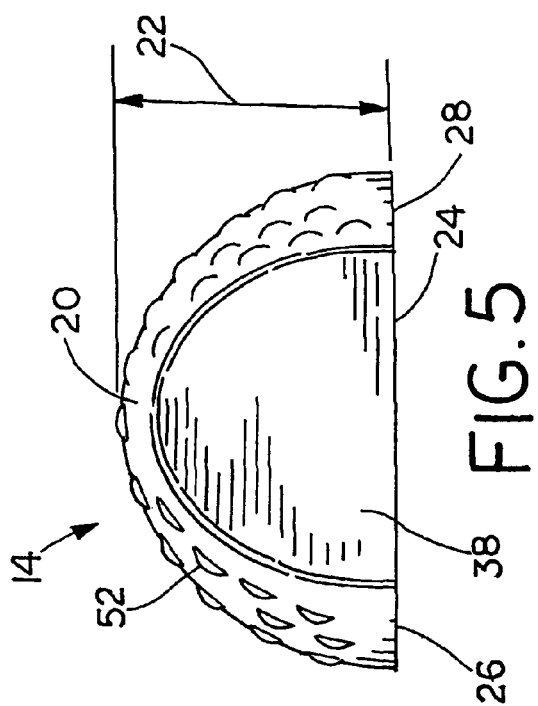
FIG. 5 is a side view of the orthopaedic cutting tool of FIG. 1.

Referring now to the drawings, and more particularly to FIGS. 1 and 2, there is shown an orthopaedic assembly 10 which generally includes a driver 12, and an orthopaedic cutting tool 14 connected to driver 12.

Driver 12 includes a shaft 16 which can be attached to a rotating tool (not shown), and a cutting tool attachment mechanism 18.

Orthopaedic cutting tool 14 (FIGS. 3-6) includes a partially hemispherical shell 20 having a shell radius 22, and a base 24 including a first circumferential base segment 26 and a second circumferential base segment 28. Shell 20 has a first part 30 on one side of first circumferential base segment 26 and second circumferential base segment 28, and a second part 32 on another side of first circumferential base segment 26 and second circumferential base segment 28. A first non-planar surface 34 is connected to first part 30, where first non-planar surface 34 has a first curvature 36 not equal to shell radius 22. A second non-planar surface 38 is connected to second part 32, where second non-planar surface 38 has a second curvature 42 not equal to shell radius 22.

First curvature 36 can include a first radius 44 which is greater than shell radius 22, for example. Second curvature 42 can include a second radius 46 which is greater than shell radius 22, for example. First radius 44 is approximately equal to second radius 46. Alternatively, first curvature 36 and/or second curvature 42 can be parabolic shaped. Cutting tool 14 can include a first curved transition 48 between first non-planar surface 34 and partially hemispherical shell 20. Further, cutting tool 14 can include a second curved transition 50 between second non-planar surface 38 and partially hemispherical shell 20. Orthopaedic cutting tool 14 can be an acetabular reamer, for shaping an acetabulum prior to the implantation of an acetabular cup during hip replacement surgery, with a plurality of cutting teeth 52 in partially hemispherical shell 20.

Different sizes of hips require different acetabular cup prosthesis, and acetabular reamers have different sizes to match a corresponding cup size. In one particular acetabular reamer, shell radius 22 can be approximately 1.0 inches, first and second radii 44, 46 can each be 1.3 inches, first and second curved transitions 48, 50 can each be 0.105 inch, and the shell 20 and first and second non-planar surfaces 34, 38 can each have a thickness of 0.020 inch. These exemplary dimensions change for different sizes of reamer 14. Also for different size reamer 14, the proportional relationship between two or more radii may stay the same, or may change.

Orthopaedic cutting tool 14 can further include a driver attachment 54 connected to base 24, where driver attachment 54 is in the form of a diametral bar with a first end 58 and a second end 60 and a centering disk 62 therebetween, and where both first end 58 and second end 60 are connected to base 24.

In use, the present invention discloses a method of reaming an acetabulum, including the steps of: providing an acetabular reamer 14 as previously described; connecting acetabular reamer 14 to driver 12; and reaming the acetabulum. The providing step can include the step of forming a first curved transition 48 between first non-planar surface 34 and partially hemispherical shell 20.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of reaming an acetabulum, comprising the steps of:

providing an acetabular reamer including a partially hemispherical shell having a shell radius, and a circumferential base including a first circumferential base segment, a second circumferential base segment, a third circumferential base segment, and a fourth circumferential base segment, said first and second circumferential base segments opposing one another and each being curved and coupled with said third and fourth circumferential base segments, said third and fourth circumferential base segments opposing one another and each being straight and coupled with said first and second circumferential base segments, said shell including a first part on one side of said first circumferential base segment and said second circumferential base segment, and a second part on another side of said first circumferential base segment and said second circumferential base segment, said third circumferential base segment forming a portion of said first part, said fourth circumferential base segment forming a portion of said second part, said acetabular reamer further including a first non-planar surface connected to said first part, said first non-planar surface having a first curvature not equal to said shell radius, and a second non-planar surface connected to said second part, said second non-planar surface having a second curvature not equal to said shell radius, said first curvature being parabolic shaped along a cross-sectional plane taken perpendicular to said third and fourth circumferential base segments and through a top dead center of said shell;

connecting said acetabular reamer to a driver; and reaming the acetabulum.

2. The method of claim 1, wherein said providing step includes the step of forming a first curved transition between said first non-planar surface and said partially hemispherical shell.

* * * * *